(12) United States Patent
Feine et al.

(10) Patent No.: US 10,449,014 B2
(45) Date of Patent: Oct. 22, 2019

(54) MOTION-ASSISTED DENTAL TREATMENT METHOD AND APPARATUS

(71) Applicant: James Feine, Bellaire, TX (US)

(72) Inventors: James Feine, Bellaire, TX (US); Mohammad A. Jamnia, Pleasant Prairie, WI (US)

( * ) Notice: Subject to any disclaimer, the term of this patent is extended or adjusted under 35 U.S.C. 154(b) by 1047 days.

(21) Appl. No.: 14/627,796

(22) Filed: Feb. 20, 2015

(65) Prior Publication Data

US 2015/0230880 A1    Aug. 20, 2015

Related U.S. Application Data

(60) Provisional application No. 61/942,142, filed on Feb. 20, 2014.

(51) Int. Cl.

| | |
|---|---|
| A61C 3/03 | (2006.01) |
| A61C 1/00 | (2006.01) |
| A61C 1/14 | (2006.01) |
| A61C 17/20 | (2006.01) |
| A61C 1/07 | (2006.01) |

(52) U.S. Cl.
CPC ............ *A61C 1/0015* (2013.01); *A61C 1/07* (2013.01); *A61C 1/148* (2013.01); *A61C 17/20* (2013.01); *A61C 3/03* (2013.01)

(58) Field of Classification Search
CPC .. A61C 3/03; A61C 1/07; A61C 1/148; A61C 17/20
See application file for complete search history.

(56) References Cited

U.S. PATENT DOCUMENTS

| | | | | |
|---|---|---|---|---|
| 5,435,032 | A * | 7/1995 | McDougall | A46B 7/06 15/201 |
| 6,453,497 | B1 * | 9/2002 | Chiang | A46B 9/10 134/6 |
| 9,642,684 | B2 * | 5/2017 | Yoshida | A46B 15/0006 |
| 2008/0318184 | A1 * | 12/2008 | Zargari | A61C 1/07 433/119 |
| 2010/0106336 | A1 * | 4/2010 | Hwang | A46B 15/0006 700/280 |
| 2014/0259472 | A1 * | 9/2014 | Bovenkamp | A61C 17/221 15/22.1 |

\* cited by examiner

*Primary Examiner* — Ralph A Lewis (74) *Attorney, Agent, or Firm* — Daniel N. Lundeen; Lundeen & Lundeen PLLC (57) ABSTRACT

Motion-assisted dental treatment method and apparatus. Manual back-and-forth manipulation of a handpiece with respect to a working surface automatically reciprocates a tip with respect to the handpiece in phase with the operator manipulation to amplify the movement of the tip adjacent the working surface and thereby attenuate the extent of hand motion required, which can help to alleviate repetitive motion fatigue. Also disclosed are motion-assisted dental treatment tools and systems for implementing the method.

20 Claims, 6 Drawing Sheets

MOTION-ASSISTED DENTAL TREATMENT METHOD AND APPARATUS

CROSS REFERENCE TO RELATED APPLICATIONS

This application is a nonprovisional of and claims the benefit of and priority to application U.S. 61/042,142, filed Feb. 20, 2014.

BACKGROUND

The statements in this section merely provide background information related to the present disclosure and may not constitute prior art.

In scaling and cleaning teeth, often clinicians depend on unpowered or hand operated scalers to scrape calculus from the teeth. Use of these instruments requires back and forth motion of the fingers, wrists and even the entire arm that may lead to fatigue, and if persisted, to potential nerve and tendon damage. To prevent fatigue, dental instruments have been made lighter to reduce the pressure of movement from the wrist area. There is a limit to weight reduction and furthermore, the need for the hand/arm movement still exists.

Other improvements have been directed to the use of powered dental instruments such as ultrasonic or vibrating scalers. This technology was first developed for drilling teeth and was later adapted to cleaning them. Use of powered instruments eliminates the need for the back and forth movement of the hand and/or entire arm. However, these instruments also require specialized training and are generally expensive and relatively heavy. Furthermore, ultrasonic instruments may adversely affect the teeth or comfort of the patient if improper power settings are used. The industry is desirous of a solution by which both the dexterity/control obtainable by an unpowered instrument, and fatigue relief obtainable by a powered instrument, may be realized.

SUMMARY

Some embodiments are directed to motion-assisted dental treatment methods. Other embodiments include motion-assisted dental treatment tools and systems. Still other embodiments are directed to reducing fatigue of an operator by employing dental tips, dental instrument systems and methods for utilizing the dental instruments disclosed herein. Further embodiments, forms, objects, features, advantages, aspects, and benefits shall become apparent from the below description and drawings.

In an embodiment, a method, e.g., to reduce fatigue on a clinician, comprises engaging a dental tip into a receiving end of a handpiece, manipulating the handpiece in reciprocation adjacent a working surface, and automatically reciprocating the dental tip with respect to the handpiece in phase with the reciprocation of the handpiece to assist movement of the tip with respect to the working surface.

In some embodiments a method comprises manipulating a handpiece receiving a dental tip, to move the dental tip adjacent to a working surface, detecting movement of the handpiece with respect to the working surface, and in response to the detected movement of the handpiece, automatically moving the dental tip with respect to the handpiece in a direction of the detected movement, thereby amplifying the movement of the of the tip adjacent to the working surface relative to the movement of the handpiece.

In an embodiment a dental scaling tool comprises a handpiece and a dental tip, wherein the dental tip comprises a normally distal working end spaced away from a normally proximal mounting end generally along a central axis, the mounting end dimensioned and arranged to releasably engage a corresponding receiving end of the handpiece, a positioning element to move the engaged dental tip relative to the handpiece, such as, for example, a reciprocating element comprising a fixed electromagnet to reciprocate the dental tip relative to the handpiece, a motion sensor to detect movement of the handpiece relative to a working surface, and a control system to operate the positioning element to move the dental tip relative to the handpiece in a direction to amplify the detected movement of the handpiece relative to the working surface.

In an embodiment, a dental treatment system comprises at least one powered dental handpiece, a non-powered dental handpiece, and a tip comprising a (normally distal) working end longitudinally separated from a (normally proximal) mounting end, the mounting end dimensioned and arranged to releasably engage a corresponding receiving end of each of the powered dental handpiece and the non-powered dental handpiece, wherein the tip is interchangeable between the powered and non-powered handpieces.

DETAILED DESCRIPTION

In the development of any such actual embodiment disclosed herein, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure.

As used in the specification and claims, "adjacent" and "near" are inclusive of "against," "at," "on," and "in." For purposes herein, a powered dental instrument includes any dental instrument which requires, in addition to any power provided by motion of the operator, another power source for operation, such as electricity from batteries or externally supplied, a motive fluid such as pressurized air, water, hydraulic fluid, or the like, or a mechanical power input. Examples include ultrasonic scalers and scrapers, and powered cutting, grinding and polishing tools, and the like.

For purposes herein, a non-powered dental instrument includes any dental instrument which is operated or engaged using only the power provided by operator manual manipulation. Examples include hand scalers, scrapers, picks, scalpels, probes (including sickle probes), scissors, clamps and the like.

In embodiments, a method to reduce fatigue on a clinician may comprise engaging a dental tip into a receiving end of a handpiece, manipulating the handpiece in reciprocation adjacent a working surface, and automatically reciprocating the dental tip with respect to the handpiece in phase with the reciprocation of the handpiece to assist movement of the tip with respect to the working surface.

In embodiments, a dental treatment method may comprise: manipulating a handpiece receiving a dental tip, to move the dental tip adjacent to a working surface; detecting movement of the handpiece with respect to the working surface; and in response to the detected movement of the handpiece, automatically moving the dental tip with respect to the handpiece in a direction of the detected movement. In such manner, the movement of the of the tip adjacent to the working surface may be amplified relative to the movement of the handpiece, or stated differently, the motion required by the operator is attenuated.

In some embodiments, the detected movement is axial, radial, angular, etc. or any combination thereof.

In some embodiments, the handpiece is powered by electrical connection to a control unit.

In some embodiments, the dental tip comprises a working end spaced away from a mounting end generally along a central axis, wherein the handpiece comprises a powered handpiece, and further comprising releasably engaging the mounting end of the dental tip in a corresponding receiving end of the powered handpiece. In some embodiments, the method may further comprise releasing the dental tip from the powered handpiece, and releasably engaging the dental tip in a corresponding receiving end of a non-powered handpiece adapted to receive the tip, and/or contacting a working surface with the tip engaged in the non-powered handpiece.

In some embodiments, the movement detection comprises receiving a signal from a motion sensor, such as an accelerometer, gyroscope, digital compass, or the like, or a combination thereof, which may be located in the handpiece or otherwise in the tool or assembly.

In some embodiments, moving the dental tip with respect to the handpiece comprises actuating an electromagnet in the handpiece. Alternatively, motors or the like may be used.

In some embodiments, the amplification has a gain of at least 20% relative to the detected movement of the handpiece, e.g., a detected 10 mm movement in the axial direction extends the tip at least 12 mm (including 2 mm extension) and/or the method may also include adjusting the gain, e.g., for operator preference.

In some embodiments, the movement of the dental tip with respect to the handpiece is a fixed distance, and/or the method may also include adjusting the fixed distance, e.g., for operator preference.

In some embodiments, a motion-assisted dental scaling tool comprises a handpiece; a dental tip comprising a working end spaced away from a mounting end generally along a central axis, the mounting end dimensioned and arranged to releasably engage a corresponding receiving end of the handpiece; a positioning element to move the engaged dental tip relative to the handpiece; a motion sensor to detect movement of the handpiece relative to a working surface; and a control system to operate the positioning element to move the dental tip relative to the handpiece in a direction to amplify the detected movement of the handpiece relative to the working surface.

In some embodiments, the positioning element moves the engaged dental tip axially in response to the detection of axial movement of the handpiece, although other movement and/or detection may be rotational, angular, or the like, or any combination.

In some embodiments, the amplification has a gain of at least 20% of the movement of the movement of the handpiece, or additionally or alternatively the displacement may be a fixed distance. In some embodiments, the control system comprises a gain or distance adjustment.

In some embodiments, the motion-assisted dental scaling tool may further comprise a retaining cap comprising a channel slideably receiving a portion of the tip, the channel having a diameter equal to or larger than a diameter of the received portion of the tip and smaller than a diameter of a locking ring radially disposed about the tip and located distally from the retaining cap, the retaining cap releasably engaged with the receiving end of the dental handpiece to retain the tip in the handpiece.

In some embodiments, the positioning element comprises a momentum transferring element, the handpiece comprising an inner cavity formed in a body having a service end and a tip receiving end, a spring disposed in the inner cavity between an electromagnet and a momentum plug, the momentum plug slideably engaged within the inner cavity between the tip receiving end and the electromagnet, the momentum plug comprising a magnetically active portion adjacent the spring and a tip attachment end receiving the mounting end of the tip.

In some embodiments, a dental treatment system comprises a powered handpiece system comprising a dental tip comprising a working end spaced away from a mounting end generally along a central axis, the mounting end dimensioned and arranged to releasably engage a corresponding receiving end of the powered handpiece; a positioning element to move a dental tip engaged therein relative to the powered handpiece; a motion sensor to detect movement of the powered handpiece relative to a working surface; and a control system to operate the positioning element to move the dental tip relative to the handpiece in a direction to amplify the detected movement of the handpiece relative to a working surface; and a non-powered dental handpiece having a receiving end to releasably engage the mounting end of the dental tip, wherein the dental tip is interchangeable between the powered and non-powered handpieces.

Figure 1:
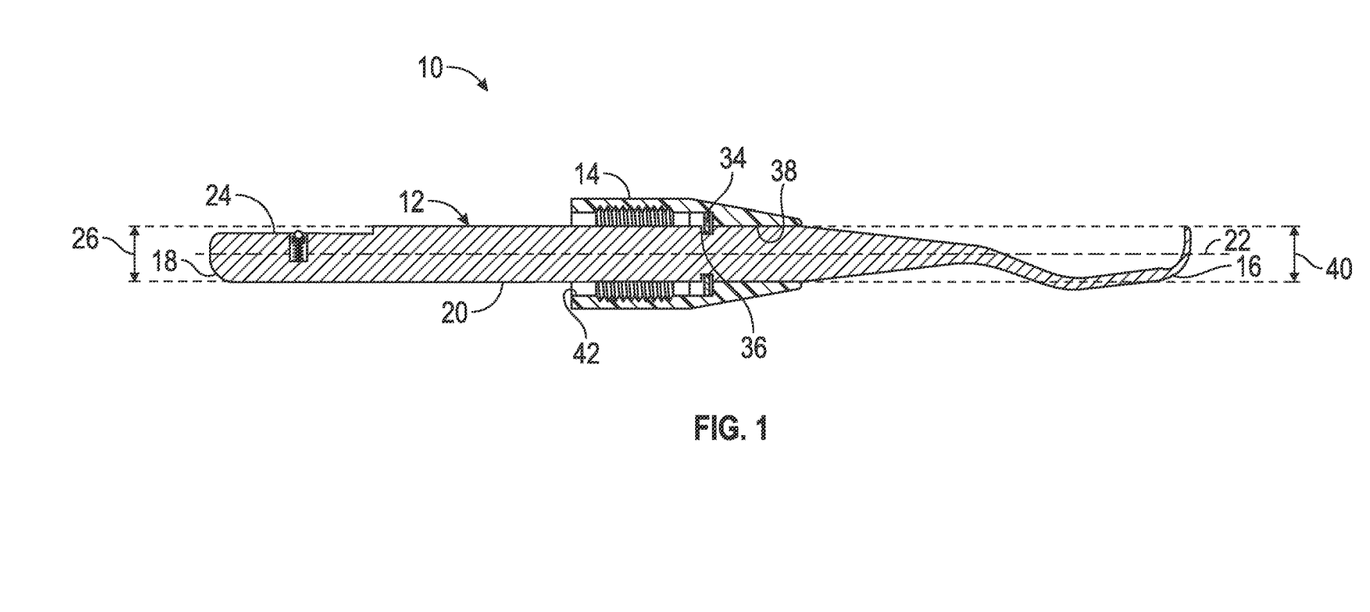
FIG. 1 is a side sectional view of a dental tip and retaining cone according to an embodiment.

With reference to the specific non-limiting embodiments shown the drawings, it is to be noted that any feature, or portion thereof, may be used in connection with any features or portions thereof shown in one or more other drawings, including any combinations and permutations thereof. In an embodiment, as shown in FIG. 1, a dental tip assembly 10 comprises an insert or tip 12 and a retaining cone 14. A normally distal working end 16 is longitudinally spaced away from a normally proximal mounting end 18 and arranged along a shank 20 having a central axis 22. In some embodiments, the mounting end 18 may be dimensioned and arranged to engage a corresponding receiving end of either or preferably both (i.e., interchangeably) a powered dental handpiece (see FIGS. 2A and 2B) and a non-powered dental handpiece (see FIG. 3).

In an embodiment, the working end 16 may comprise any number of shapes and/or arrangements for scaling and other dental practitioner tools, readily known to one of skill in the art. As used herein, dental practitioner refers not only to dental hygienists, but also to dentists, oral surgeons, their nurses, nurse practitioners, technicians and other assistants, and the like. Examples of suitable tip designs include the various "Gracey®" designs, Banhard® designs, McCall® designs, sickles, UC Rule® designs, US Ratcliff® designs, Moser® designs, Jacquettes® designs, Prichard® designs, Rhodes-Chisel® designs, Hirschfeld® designs, Younger-Good® designs, Goldman-Fox® designs, Morse® designs, and the like.

Figure 3:
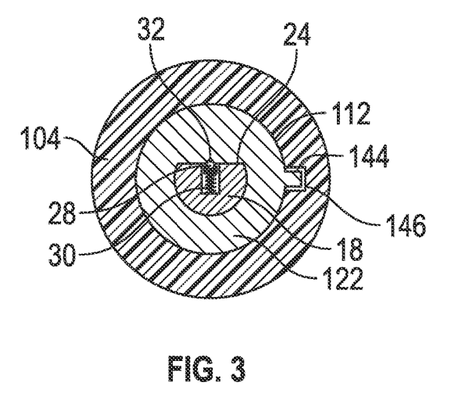
FIG. 3 is a cross-sectional view of the powered dental tool assembly of FIG. 2A as seen along the lines 3-3.

In an embodiment, the mounting end 18 comprises a "D" profile with a flat or planar portion 24 which is complimentary to a corresponding receiving end of a powered and/or non-powered dental handpiece in a tool assembly. In an embodiment, a diameter 26 of the shank 20 at the mounting end 18 may be dimensioned to provide frictional engagement with a corresponding receiving end of a powered or non-powered dental handpiece and/or a cross-sectional shape of the mounting end 18 may be dimensioned and arranged to provide both engagement and positioning of the dental tip 12 within a corresponding receiving end of a powered or non-powered dental handpiece. For example, in an embodiment, a portion of the mounting end 18 may have a "D" shaped cross-section as shown, although any non-circular profile may be used to maintain rotational alignment between the tip 12 and the handpiece, such as, for example, a triangular, square, pentagonal, hexagonal or other polygonal cross section, a spline or keyway, grooves or ridges, or the like, or any combination thereof. Additionally and/or alternatively, as best seen in FIG. 3, a ball 28 may be radially biased, either inwardly or outwardly as shown, by spring 30 into an opposing detent 32.

In an embodiment, the dental tip 12 may further comprise a stop element such as locking ring 34 which may be formed integrally with the tip 12 or may be received at least partially within a receiving element such as a radial groove 36 formed in a surface of the dental tip. In an embodiment, the dental tip 12 may be removably secured into a dental handpiece using a retaining element such as cone 14 having a distal bore 38 with an inside diameter 40 smaller than a diameter of the locking ring 34 to locate the locking ring proximally and the working end 16 distally with respect to the distal bore 38 of the cone. As used herein, "distal" refers to the end or direction of the tool or component at or toward the working end 16 of the tool away from the operator and/or near the patient or working element, and "proximal" refers to the end or direction of the tool or component near the operator and/or away from the patient or working element.

In an embodiment, the tip 12 is at least partially slideably received, e.g., the tip 12 is at least partially longitudinally and/or partially rotationally slideable within the bore 38, which may have a diameter 40 which is equal to or larger than the shank diameter 26 and smaller than an outside diameter of the locking ring 34. In this manner, the cone 14 may cooperate with the locking ring 34 to retain the tip 12 within a handpiece and/or limit the forward axial movement of the tip 12 with respect to the cone 14.

In an embodiment, the retaining cone 14 may further comprise an inner surface 32 dimensioned and arranged to releasably engage a complementary receiving end of various different handpieces, e.g., both the powered and non-powered dental handpieces described herein. In an embodiment, the inner surface 42 comprises threads for threaded engagement with, for example, one or more complementarily threaded dental handpieces.

Figure 2A:
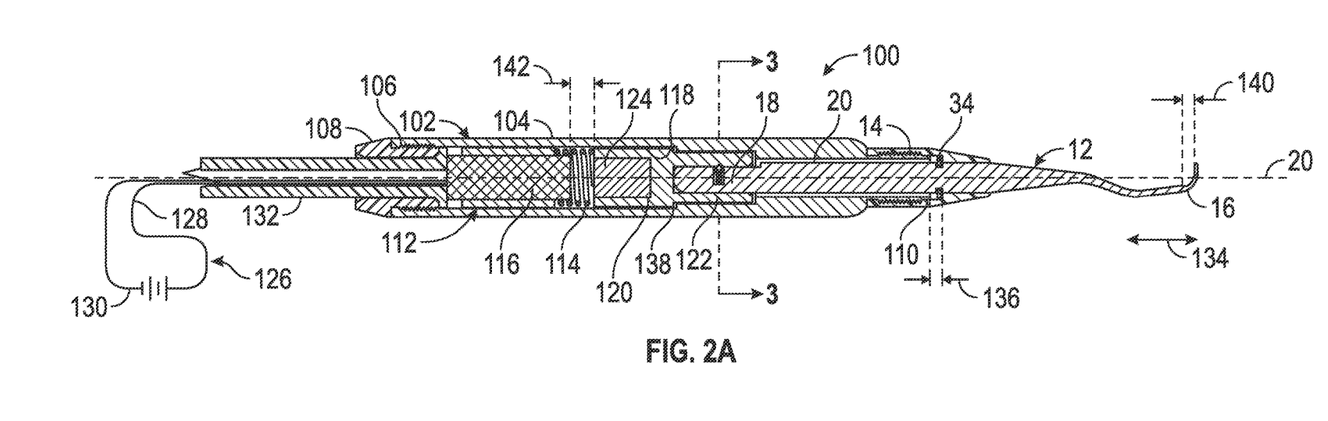
FIG. 2A is a side sectional view of a powered dental tool assembly according to an embodiment.
Figure 2B:
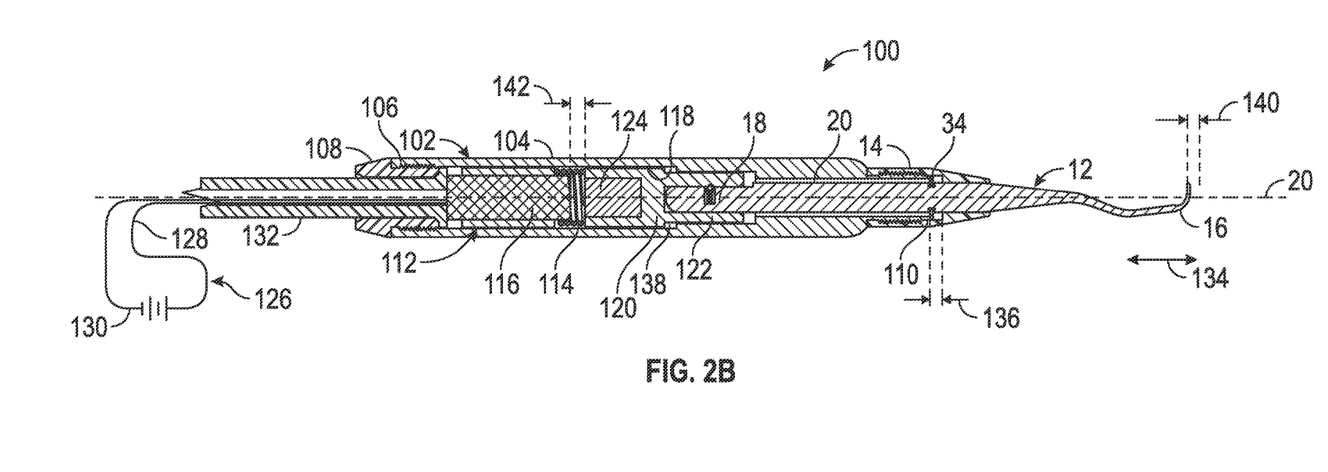
FIG. 2B is a side sectional view of the powered dental tool assembly of FIG. 2A with tip moved inwardly.

The embodiment shown in FIGS. 2A-2B depicts an assembled dental tool 100 wherein the dental tip 12 is dimensioned and arranged for releasable engagement with a powered dental handpiece 102, e.g., via the retaining cone 14. In an embodiment, the handpiece 102 is a momentum transferring non-ultrasonic handpiece comprising a body 104 having an internally threaded proximal end 106 to receive end plug 108 and an externally threaded distal end 110 to engage the cone 14. In an embodiment, an inner cavity 112 houses a spring 114 is disposed between an electromagnet 116 which may be positionally fixed and a momentum plug 118 which may be slideable within at least a portion of the inner cavity 112, e.g., rotationally and/or longitudinally.

In an embodiment, the momentum plug 118 is elongated coaxially along central axis 20, comprising an enlarged proximal end 120 and a distal end 122 with a narrowed outside diameter for sliding longitudinally within the complementarily shaped cavity 112. In an embodiment, the momentum plug 118, or at least a portion thereof, may be made of a magnetically susceptible material for attraction to the electromagnet 116 when it is activated, and may alternatively and/or additionally comprise a magnet 124, e.g., in the proximal end 120 adjacent the electromagnet 112.

In an embodiment, the electromagnet 116, the spring 114 and the momentum plug 118 are dimensioned and arranged such that application of a current via circuit 126 from control unit 127 to the electromagnet 116, e.g., through conductors 128 and 130 arranged in a cable 132 through the end plug 108, energizes the electromagnet 116 to attracts the momentum plug 118 to compress the spring 114 and move the tip 10 longitudinally along the central axis 20. Upon termination and/or reversing of the current the spring 114 biases the momentum plug 118 back to a distally forward position. Accordingly, in an embodiment, supply of pulsed electric current and/or an alternating electric current to the electromagnet 116 results in a generally longitudinal oscillation or reciprocation 134 of the momentum plug 118 and by extension, the tip 10 with respect to the handpiece 102 of the tool assembly 100.

In an embodiment, the tip 10 has a linear motion range 136 that is limited distally by the cone 14 interengaging the locking ring 34 as mentioned above, and/or by the shoulder abutment 138 between the opposing annular surfaces of the momentum plug 118 and the cavity 112 at the transition between the enlarged and narrowed portions. The proximal extent of the motion range 136 may be limited by the extent of compression of the spring 114 against the electromagnet 116, and/or by the locking ring 34 against the handpiece body end 136. The range of motion 140 of the distal end and the delta of the spring compression 142 between FIGS. 2A and 2B I similar to that of range 136. In an embodiment, the distal end 16 of the tip 12 has a linear range of motion 140 that is from about 0.1 to about 10 mm, or from about 0.1 to 5 mm, or from about 0.1 to 1 mm, or from about 1 to about 5 mm.

In some embodiments the range of motion 140 can also be adjusted to suit operator preference, e.g., via a control circuit (see FIG. 7) and/or mechanically by adjusting the location of the locking ring and/or employing annular spacer elements such as washers (not shown) as desired on either side of the locking ring 34, proximally to limit proximal travel and/or distally to limit distal travel.

In an embodiment, the rate of oscillation of the tip 12, where the oscillation amplifies the motion of the tip 12 at a working surface relative to the handpiece 102, generally matches that of the operator in generating back and forth motion of the handpiece 102, i.e., the oscillation of the tip 12 is responsive in phase with the oscillation of the handpiece 102. If desired, a secondary oscillation or vibration may be imparted to the tip 12, where the frequency of the secondary oscillation is greater than that of the reciprocation of the handpiece 102, e.g., at least 10 times greater or 100 times greater, but the range of motion of the secondary oscillation is substantially less than the full range of motion 140 of the tip 12, e.g., less than 20%, less than 10% or less than 5% of the full range of motion. In an embodiment, the rate of secondary oscillation 134 is below the ultrasonic range of 10,000 Hz, e.g., infrasonic. In an embodiment, the rate of secondary oscillation of the tip is between about 0.1 and 100 Hz, or between about 0.5 and 20 Hz, or between about 1 and 10 Hz, or between about 2 and 8 Hz, or about 4 to about 5 Hz. Accordingly, the primary oscillation of the tip upon activation of the electromagnetic coil is similar to the motion and rate utilized by an entirely manual hand operated or non-powered dental handpiece. As such, the powered dental tool according to the instant disclosure may relieve a portion or a major portion of the strain and fatigue experienced by the operator employing the handpiece to clean a surface. By mimicking and/or slightly improving the range of motion and rate of oscillation employed by an operator utilizing a non-powered dental tool, the powered tool reduces some of the fine movement strain otherwise experienced by the operator.

In some embodiments, the reciprocation of the tip 12 may be operatively linked in phase to the motion imparted by the clinician to the handpiece 102, thereby providing a motion assist to attenuate the movement needed by the clinician to effect the desired extent of travel of the tip adjacent the tooth or other work surface. For example, the reciprocation can be associated with a motion sensor (see FIG. 7) such as an accelerometer, gyroscope, digital compass, or the like, or a combination thereof, which may activate the electromagnet 116 to attract or repel the magnet 124 and thereby effect relative movement of the tip 12. Microelectronic mechanical systems (MEMS) accelerometers are well known and are commercially available, e.g., ultra-low-power high-performance 1-, 2-, 3- and/or 6-axis linear accelerometers, e.g., belonging to the femto family, with digital (e.g. I2C, SPI and/or serial interface) or analog output, wake-up function, and the like, are available under the trade designations ANALOG DEVICES, BOSCH SENSORTEC, FREESCALE SEMICONDUCTOR, GRAVITECH, STIMIRO-ELECTRONICS, KIONIX, KNOWLES, MCUBE, MEASUREMENT SPECIALTIES, MURATA, PANASONIC, PARALLAX, ROHM SEMICONDUCTOR, and the like. Accelerometers can be small, e.g., 2×2×1 mm, and can have sensitivities on the order of 0.1-100 mg/digit or LSB, or 0.01-2 V/g or the like. MEMS motion sensors that may be employed include, for example, accelerometers, gyroscopes, digital compasses, and combinations thereof.

In some embodiments, the full length of reciprocation can be triggered by detecting a change in direction of movement of the handpiece 102, and if desired the speed of the reciprocation can be controlled, i.e., the time it takes the tip 12 to travel the full range of motion 140 can be determined by gradually or controllably changing the voltage to the electromagnet 116, employing a damper mechanism (not shown), or the like. In other embodiments, the reciprocation of the tip 12 can be advanced proportionally in response to the magnitude of motion of the handpiece 102 that is detected. In some embodiments, the displacement of the tip 12 can be at least 20% of the magnitude of detected motion of handpiece 102, i.e., the "gain" is at least 20%, e.g., 30% or more, 50% or more, 100% or more, or 200% or more.

If desired, rotational alignment and/or rotation of the plug 118 (and thus the tip 10) may be facilitated by a cooperating arrangement of a spline and channel and/or pin 144 and channel 146 between the plug 118 and an inner surface of the cavity 112, as seen in FIG. 3. In this manner, by fixing the radial direction of the pin 144/channel 146, the reciprocation of the plug/tip assembly may impart some rotational movement to the distal end of the tip to help relieve operator strain resulting from a twisting movement of the tool 100.

Figure 4:
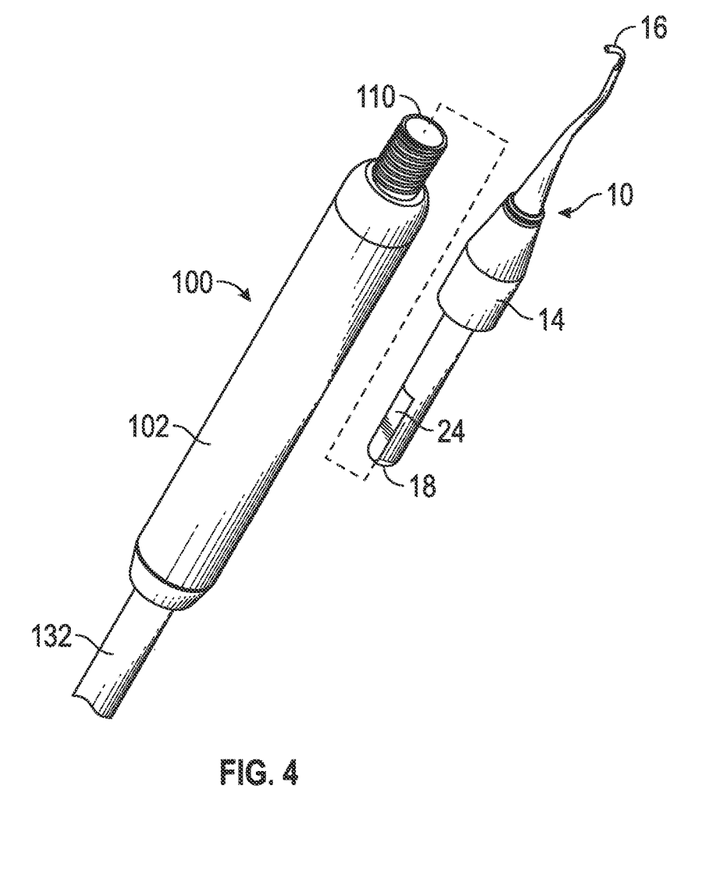
FIG. 4 is a side sectional view of a non-powered dental tool assembly according to an embodiment.
Figure 5:
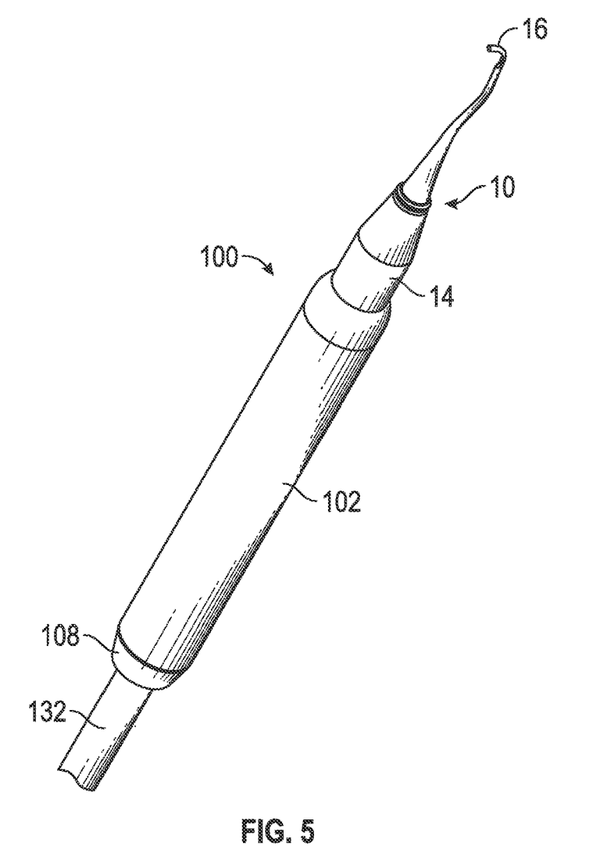
FIG. 5 is an exploded view of a powered dental tool assembly according to an embodiment.
Figure 6:
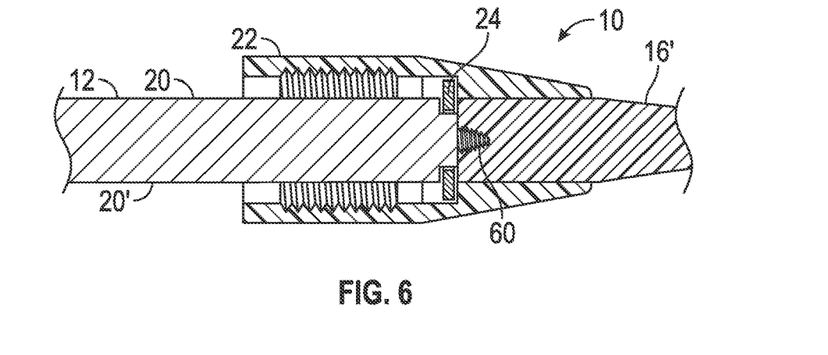
FIG. 6 is a perspective view of a powered dental tool assembly according to an embodiment.

FIG. 4 shows an exploded perspective view of an embodiment of the powered tool 100 shown in FIGS. 2A-2B with a tip 12 and handpiece assembly 102. FIG. 5 shows a perspective view of the embodiment of the fully assembled powered handpiece 100.

Where the tip 12 is manufactured wholly or partially from a magnetically susceptible material, the magnetic susceptibility of at least the proximal end 18 and/or the shank 20 may facilitate retention of the tip 12 in the momentum plug 118 (or plug 314 in FIG. 7 discussed below). On the other hand, where the working distal end of the tip 12 is made of a non-magnetic material, materials such as plastic may be selected for cleaning surfaces such as implants that might otherwise be susceptible to damage when a metallic tip material is employed. In an embodiment illustrated in FIG. 6, a non-magnetic distal portion 16' is secured to the magnetic portion 20', e.g., by threaded engagement at 60, although other attachment means such as glue, clamps, etc. could also be employed.

Figure 7:
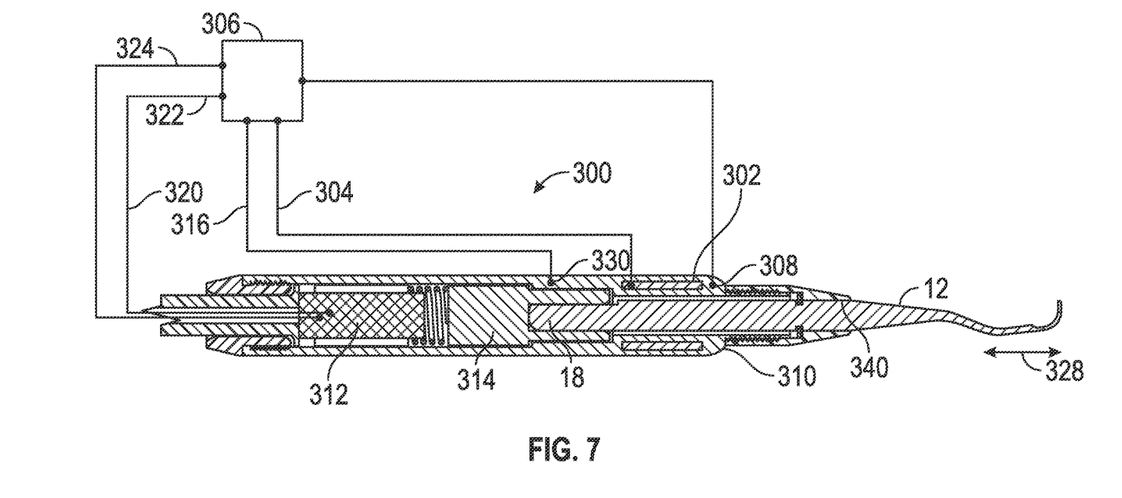
FIG. 7 is a side sectional view of a powered dental tool assembly and control system according to another embodiment.

In an embodiment as shown in FIG. 7, the powered handpiece assembly 300 is similar to the embodiment of FIGS. 2A-2B, but may further include at least one secondary coil 302 in electronic communication with a control unit 306. In an embodiment, one or more secondary coil(s) 302 is (are) dimensioned, arranged, and/or configured such that movement of the (magnetized) tip 12 and/or the momentum plug 314 induces an electrical current in secondary coil 302. In an embodiment, the control unit 306 comprises circuitry and/or logic suitable to monitor states, activations, and variations of this induced current. In an embodiment, control unit 306 is also capable of increasing and/or reducing power via circuit 320 to the coil of the electromagnet 312 in response to feedback from the secondary coil 302 to assist the clinician when it is sensed that more or less power is needed to maintain movement of the tip 12, e.g., when the operator applies more force to press the distal end of the tip against the tooth surface, as in removing more stubborn calculus, thereby limiting movement of the tip 12 which is sensed as requiring more power to obtain the desired extent of movement; and/or the control unit 306 may be capable of reducing the power via current 320 to the coil of the electromagnet 312 based on the induced magnetic field 308 to thereby reduce the power transferred to the tip 10 should the tip be removed from a tooth surface or held only relatively lightly against a particular tooth surface which may be relatively clean.

In an embodiment, one or more additional sensors 308 and/or 330, in electronic communication (including wireless, sonic, optical, etc.) with control unit 306 may be utilized. The sensor(s) 308 and/or 330 are shown located in an outer housing near the distal end of the handpiece 310 and approximately medially, respectively, but it is to be understood that one or more of the sensors 308 and/or 330 may be located anywhere in, on or proximate to the powered handpiece assembly 300.

Figure 9:
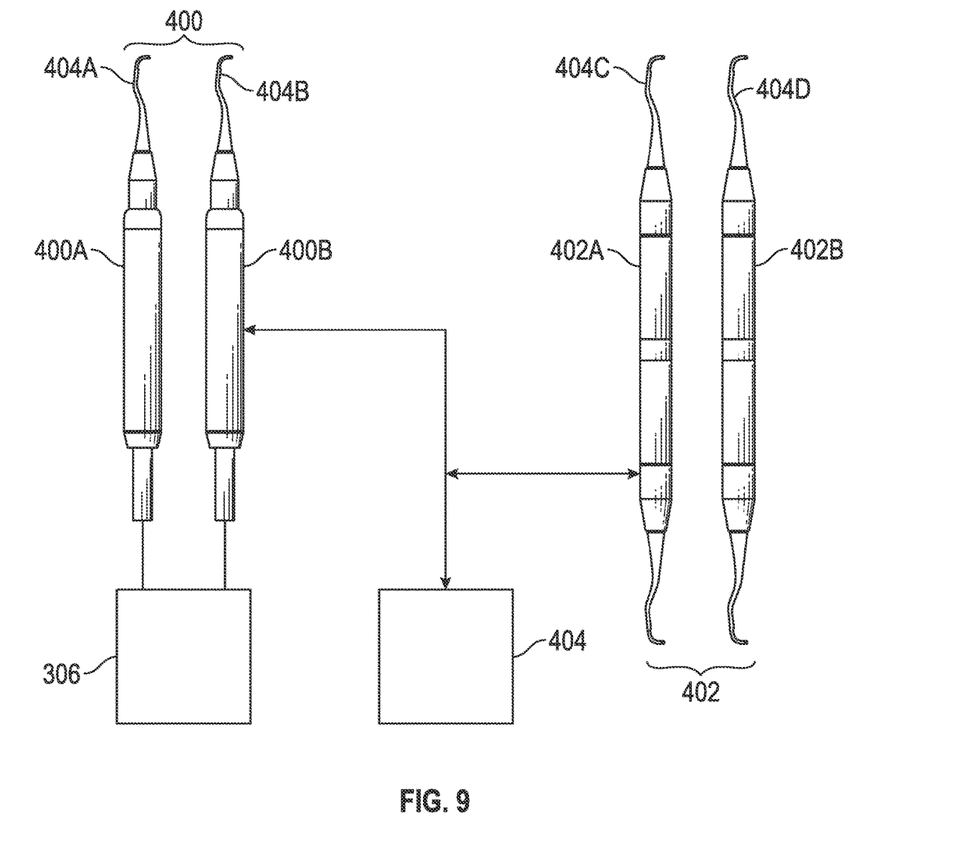
FIG. 9 is a side sectional view of a dental tool with a composite tip construction according to another embodiment.

In an embodiment, sensor(s) 308 and/or 330 may include a touch sensor for use in an embodiment in which a plurality of powered hand pieces are employed in cleaning a particular surface (see. FIG. 9). A plurality of handpieces may be needed to assist clinicians. As is known to one of skill in the art, clinicians and other operators generally utilize several two-headed non-powered hand pieces while performing a cleaning or other procedure on a patient. The plurality of two-headed non-powered hand pieces typically include two tips, one designed to be used, for example, on the buccal side of the tooth and the other designed to be used on the lingual side. A clinician generally flips the instrument in her/his hand to work on the lingual or buccal side of the tooth. To provide the same functionality to the clinicians, in an embodiment, at least two powered hand pieces may be provided, e.g., one having a tip useful for the buccal side of a tooth and the other having a tip useful for the lingual side of a tooth. This arrangement allows the clinician to switch between the two powered handpieces while performing the cleaning procedure without wasting the time needed to change the tips in the same powered handpiece.

The touch sensor(s) 308 and/or 330 where provided may allow the control unit to sense which handpiece the operator is using, for example. When a multiplicity of powered hand pieces are each attached to the same base unit, only one handpiece should be energized at any given time. Accordingly, in an embodiment, a touch sensor(s) 308 and/or 330, which may be a capacitive sensing mechanism, a pressure sensitive switch, and/or the like, may be utilized to signal the base unit 306 as to which of the plurality of attached handpieces is being utilized and thus, which of the plurality of attached handpieces is to receive power and/or be monitored and/or controlled at any given moment.

In an embodiment, the sensor(s) 308 and/or 330 may include a thermocouple, chemical sensor, a motion sensor and/or the like. In an embodiment, sensor(s) 308 and/or 330 may include a motion sensor, such as an accelerometer, gyroscope, digital compass, or the like, or a combination thereof, in electronic communication with the control unit 306 to allow for monitoring of the directionality and acceleration of the handpiece in order to adjust operational conditions such as the oscillation frequency and/or power supplied to the handpiece which facilitates the operator and in-turn reduces fatigue and other operational concerns.

In an embodiment, tip 12 may further comprise an identification tag 340, readable by an electronic sensor in proximity thereto in direct or indirect communication with the control unit 306. In an embodiment, identification tag 340 may include an RFID or other electronically readable component. In an embodiment, the control unit 306 and/or sensor(s) 308 and/or 330 may further include a reader to sense the tag 340. In an embodiment, the reader may be utilized to identify the configuration of the working end of tip 12, and thereby to provide power to the electromagnet 312 and/or provide an appropriate amplitude (level of linear motion 328) and/or power based on predefined standards or algorithms. In an embodiment, the power provided to the electromagnet 312 and/or the appropriate level of linear motion 328 of tip 12 is based on predefined standards or algorithms which are further modified according to predefined standards of the particular operator conducting the cleaning as sensed by the control unit or as input into the control unit, and/or the particular needs of the particular patient receiving the cleaning or other procedure as sensed by the control unit or as input into the control unit.

In an embodiment, the sensing element 316 may be utilized in conjunction with the control unit 306 to provide a tip-based computer-controlled system for the powered handpiece as disclosed in U.S. Pat. No. 8,204,612, U.S. Patent publication 2013/0045456, and progeny, all of which are incorporated by reference herein.

Figure 8:
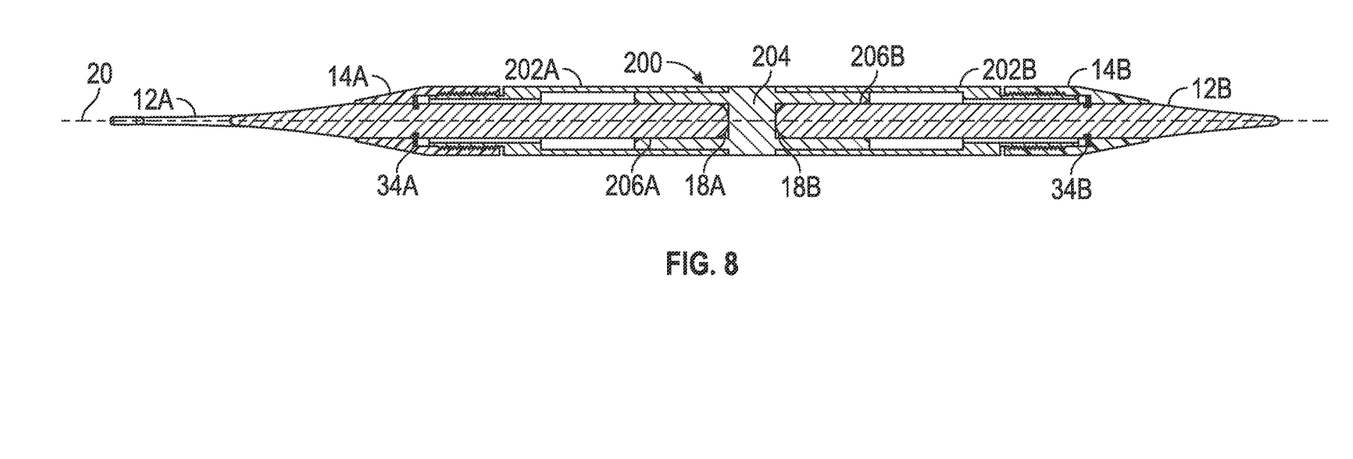
FIG. 8 is a schematic diagram of a dental hygiene system according to an embodiment.

In addition, by allowing the operator to utilize the same tip in both powered and non-powered tools, the dental treatment system according to the instant disclosure enables the operator to select the desired mode for cleaning a particular surface according to the needs and conditions of the patient and/or clinician. In an embodiment, as shown in FIG. 8, the two dental tips 12A and 12B are dimensioned and arranged to be releasably engaged in either end 202A, 202B of the non-powered dental handpiece 200. In an embodiment, the retaining cones 14A, 14B engage and bias the locking rings 34A, 34B inwardly (proximally), bottoming the distal ends 18A, 18B of the tips 12A, 12B into contact with center plug 204, which has a complimentarily profiled (D-shaped) cross section in each opposing receiving well 206A, 206B.

Non-powered tool 200 may thus be provided with tips at either end, which may be mirror image tips, for example, for working on teeth in different areas of the patient's mouth or with different approaches to the teeth, e.g., top or bottom, forward or back teeth, on the left or right side and/or inside and outside surfaces. The operator can turn the tool around to use the opposite end and thus quickly prepare for differently oriented working surfaces. In an embodiment herein, a similar functionality may be provided by powering a plurality of the powered handpieces from one power supply or generator, e.g., a first handpiece fitted with a first tip and connected to the generator with a first power cable, a second handpiece fitted with a second tip and connected to the generator with a second power cable, and so on (see FIG. 9). In this manner, the operator may have the two different or mirror-image tips at the ready to facilitate a rapid selection while working different techniques or areas of the working surfaces.

In an embodiment as shown in FIG. 9, a dental treatment system comprises an inventory 400 comprising a plurality of powered dental handpieces 400A, 400B and so on, a control unit 306, an inventory 402 comprising one or more non-powered dental handpieces 402A, 402B and so on, and an inventory 404 including at least a plurality of tips 404A, 404B, 404C, 404D and so on, according to any one or combination of embodiments disclosed herein. In an embodiment, the tips in tip inventory 404 may be used interchangeably in any of the handpieces in inventories 400, 402, i.e., with either manual or powered handpieces.

In an embodiment, a method comprises engaging a dental tip in a receiving end of a powered dental handpiece or a non-powered dental handpiece according to any one or combination of embodiments or systems disclosed herein, and contacting a surface with the dental tip thereby cleaning the surface, wherein the dental tip comprises a working end longitudinally separated from a mounting end, the mounting end dimensioned and arranged to releasably engage a corresponding receiving end of both the powered dental handpiece and the non-powered dental handpiece.

In an embodiment, a method to reduce fatigue on a clinician comprises engaging a dental tip in a receiving end of a powered dental handpiece or a non-powered dental handpiece according to any one or combination of embodiments or systems disclosed herein, and contacting a surface with the dental tip thereby cleaning the surface, wherein the dental tip comprises a working end longitudinally separated from a mounting end, the mounting end dimensioned and arranged to releasably engage a corresponding receiving end of both the powered dental handpiece and the non-powered dental handpiece.

In an embodiment, a method to reduce fatigue on a clinician comprises engaging a plurality of dental tips into a corresponding plurality of receiving ends of powered dental hand pieces or a non-powered dental hand pieces each according to any one or combination of embodiments or systems disclosed herein, and contacting a surface with at least one of the plurality of dental tips thereby cleaning the surface, wherein each of the dental tips comprise a working end longitudinally separated from a mounting end, the mounting end dimensioned and arranged to releasably engage a corresponding receiving end of both the powered dental handpiece and the non-powered dental handpiece.

EMBODIMENTS LISTING

Accordingly, the instant disclosure provides the following embodiments:

A. A method to reduce fatigue on a clinician comprising:
  manipulating a handpiece receiving a tip in reciprocation adjacent a working surface; and
  automatically reciprocating the dental tip with respect to the handpiece in phase with the reciprocation of the handpiece to assist movement of the tip with respect to the working surface.
B. The method of embodiment A, further comprising engaging the dental tip into a receiving end of the handpiece.
C. The method of embodiment A or embodiment B further comprising detecting movement of the handpiece with respect to the working surface.
D. The method of embodiment C, further comprising in response to the detected movement of the handpiece, automatically moving the dental tip with respect to the handpiece in a direction of the detected movement, thereby amplifying the movement of the of the tip adjacent to the working surface relative to the movement of the handpiece.
E. A dental treatment method, comprising:
  manipulating a handpiece receiving a dental tip, to move the dental tip adjacent to a working surface;
  detecting movement of the handpiece with respect to the working surface; and
  in response to the detected movement of the handpiece, automatically moving the dental tip with respect to the handpiece in a direction of the detected movement, thereby amplifying the movement of the of the tip adjacent to the working surface relative to the movement of the handpiece.
F. The dental treatment method of embodiment D or embodiment E, wherein the detected movement is axial.
G. The dental treatment method of any one of embodiments D to F, wherein the detected movement is radial.
H. The dental treatment method of any one of embodiments D to G, wherein the handpiece is powered by electrical connection to a control unit.
I. The dental treatment method of any one of embodiments D to H, wherein the dental tip comprises a working end spaced away from a mounting end generally along a central axis, wherein the handpiece comprises a powered handpiece, and further comprising releasably engaging the mounting end of the dental tip in a corresponding receiving end of the powered handpiece.
J. The dental treatment method of embodiment I, further comprising releasing the dental tip from the powered handpiece, and releasably engaging the dental tip in a corresponding receiving end of a non-powered handpiece adapted to receive the tip.
K. The dental treatment method of any one of embodiments D to J, wherein the movement detection comprises receiving a signal from an motion sensor, such as an accelerometer, gyroscope, digital compass, or a combination thereof, in the handpiece.
L. The dental treatment method of any one of embodiments D to K, wherein moving the dental tip with respect to the handpiece comprises actuating an electromagnet in the handpiece.
M. The dental treatment method of any one of embodiments D to L, wherein the amplification has a gain of at least 20% relative to the detected movement of the handpiece, preferably 30% or more, 50% or more, 100% or more, or 200% or more.
N. The dental treatment method of embodiment M, further comprising adjusting the gain.
O. The dental treatment method of any one of embodiments D to N, wherein the movement of the dental tip with respect to the handpiece is a fixed distance.
P. The dental treatment method of embodiment 0, further comprising adjusting the fixed distance.
Q. A motion-assisted dental scaling tool, comprising:
  a handpiece;
  a dental tip comprising a working end spaced away from a mounting end generally along a central axis, the mounting end dimensioned and arranged to releasably engage a corresponding receiving end of the handpiece;
  a positioning element to move the engaged dental tip relative to the handpiece;
  a motion sensor to detect movement of the handpiece relative to a working surface; and
  a control system to operate the positioning element to move the dental tip relative to the handpiece in a direction to amplify the detected movement of the handpiece relative to the working surface.
R. The motion-assisted dental scaling tool of embodiment Q, wherein the positioning element axially moves the engaged dental tip in response to the detection of axial movement of the handpiece.
S. The motion-assisted dental scaling tool of embodiment Q or embodiment R, wherein the positioning element radially moves the engaged dental tip in response to the detection of axial movement of the handpiece.
T. The motion-assisted dental scaling tool of any one of embodiments Q to S, wherein the amplification has a gain of at least 20% of the movement of the movement of the handpiece, preferably 30% or more, 50% or more, 100% or more, or 200% or more.
U. The motion-assisted dental scaling tool of any one of embodiments Q to T, wherein the movement of the tip with respect to the handpiece is a fixed distance.
V. The motion-assisted dental scaling tool of any one of embodiments Q to U, wherein the control system comprises a gain or fixed distance adjustment.
W. The motion-assisted dental scaling tool of any one of embodiments Q to V, further comprising a retaining cap comprising a channel slideably receiving a portion of the tip, the channel having a diameter equal to or larger than a diameter of the received portion of the tip and smaller than a diameter of a locking ring radially disposed about the tip and located distally from the retaining cap, the retaining cap releasably engaged with the receiving end of the dental handpiece to retain the tip in the handpiece.

X. The motion-assisted dental scaling tool of any one of embodiments Q to W, wherein the positioning element comprises a momentum transferring element, the handpiece comprising an inner cavity formed in a body having a service end and a tip receiving end, a spring disposed in the inner cavity between an electromagnet and a momentum plug, the momentum plug slideably engaged within the inner cavity between the tip receiving end and the electromagnet, the momentum plug comprising a magnetically active portion adjacent the spring and a tip attachment end receiving the mounting end of the tip.

Y. A dental treatment system comprising:
a powered handpiece system comprising a dental tip comprising a working end spaced away from a mounting end generally along a central axis, the mounting end dimensioned and arranged to releasably engage a corresponding receiving end of the powered handpiece; a positioning element to move a dental tip engaged therein relative to the powered handpiece; a motion sensor to detect movement of the powered handpiece relative to a working surface; and a control system to operate the positioning element to move the dental tip relative to the handpiece in a direction to amplify the detected movement of the handpiece relative to a working surface; and
a non-powered dental handpiece having a receiving end to releasably engage the mounting end of the dental tip, wherein the dental tip is interchangeable between the powered and non-powered handpieces.

Accordingly, in an embodiment, the dental treatment system comprises a system to sense the conditions of operation and a control/feedback mechanism which adjusts the operation of the powered dental handpiece according to the environment to facilitate the operator and thus reduce the fatigue and stress required by the operator to perform the cleaning of the dental surface, while also allowing the operator to utilize the same tip or set of tips in a manual or hand-operated handpiece to further facilitate cleaning of the dental surface according to the requirements of the patient.

The foregoing disclosure and description of the invention is illustrative and explanatory thereof and it can be readily appreciated by those skilled in the art that various changes in the size, shape and materials, as well as in the details of the illustrated construction or combinations of the elements described herein can be made without departing from the spirit of the invention.

While the invention has been illustrated and described in detail in the drawings and foregoing description, the same is to be considered as illustrative and not restrictive in character, it being understood that only some embodiments have been shown and described and that all changes and modifications that come within the spirit of the inventions are desired to be protected. It should be understood that while the use of words such as preferable, preferably, preferred, more preferred or exemplary utilized in the description above indicate that the feature so described may be more desirable or characteristic, nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method to reduce fatigue on a clinician comprising:
engaging a mounting end of a dental scaling tip into a receiving end of a handpiece, wherein the mounting end of the tip is releasably engaged in the receiving end of the handpiece, wherein a working end of the tip is spaced away from and fixed in position relative to the mounting end generally along a central longitudinal axis of the bandpiece;
manipulating the handpiece in reciprocation adjacent a working surface; and
automatically reciprocating the mounting end of the tip with respect to the handpiece in phase with the reciprocation of the handpiece to amplify movement of the working end of the tip with respect to the working surface, wherein the reciprocation of the mounting end of the tip with respect to the handpiece is advanced proportionally in response to a magnitude of the reciprocation of the handpiece relative to the working surface.

2. A dental treatment method, comprising:
manipulating a handpiece receiving a mounting end of a dental scaling tip to move a working end of the tip adjacent to a working surface, wherein the working end of the tip is spaced away from and fixed in position relative to the mounting end generally along a central longitudinal axis of the handpiece;
detecting movement of the handpiece with respect to the working surface; and
in response to the detected movement of the handpiece, automatically moving the mounting end of the tip with respect to the handpiece in a direction of the detected movement, thereby amplifying the movement of the of the working end of the tip adjacent to the working surface relative to the movement of the handpiece wherein the movement of the mounting end of the tip relative to the handpiece is proportional to a magnitude of the detected movement of the handpiece;
wherein movement of the of the working end of the tip adjacent to the working surface removes scale from the working surface.

3. The dental treatment method of claim 2, wherein the detected movement is axial.

4. The dental treatment method of claim 2, wherein the detected movement is radial.

5. The dental treatment method of claim 2, wherein the handpiece is powered by electrical connection to a control unit.

6. The dental treatment method of claim 2, wherein the handpiece comprises a powered handpiece, and further comprising releasably engaging the mounting end of the dental tip in a corresponding receiving end of the powered handpiece.

7. The dental treatment method of claim 6, further comprising: releasing the mounting end of the tip from the powered handpiece; releasably engaging the mounting end of the tip in a corresponding receiving end of a non-powered handpiece adapted to receive the mounting end of the tip;

and manipulating the non-powered handpiece to move the working end of the tip in fixed relation to the non-powered handpiece.

8. The dental treatment method of claim 2, wherein the movement detection comprises receiving a signal from a motion sensor in the handpiece.

9. The dental treatment method of claim 2, wherein moving the dental tip with respect to the handpiece comprises actuating an electromagnet in the handpiece.

10. The dental treatment method of claim 2, wherein the amplification has a gain of at least 20% relative to the detected movement of the handpiece.

11. The dental treatment method of claim 10, further comprising adjusting the gain.

12. The dental treatment method of claim 2, wherein the movement of the mounting end of the tip with respect to the handpiece is a fixed distance.

13. The dental treatment method of claim 12, further comprising adjusting the fixed distance.

14. A motion-assisted dental scaling tool, comprising:
a handpiece;
a dental tip comprising a working end spaced away from and fixed in position relative to a mounting end generally along a central axis, the mounting end dimensioned and arranged to releasably engage a corresponding receiving end of the handpiece;
a positioning element to move the engaged mounting end of the tip relative to the handpiece;
a motion sensor to detect movement of the handpiece relative to a working surface; and
a control system to operate the positioning element to move the mounting end of the tip relative to the handpiece in a direction to amplify movement of the working end proportional to the detected movement of the handpiece relative to the working surface.

15. The motion-assisted dental scaling tool of claim 14, wherein the positioning element axially moves the engaged dental tip in response to the detection of axial movement of the handpiece.

16. The motion-assisted dental scaling tool of claim 14, wherein the amplification has a gain of at least 20% of the movement of the handpiece.

17. The motion-assisted dental scaling tool of claim 14, wherein the control system comprises a gain or distance adjustment.

18. The motion-assisted dental scaling tool of claim 14, further comprising a retaining cap comprising a channel slideably receiving a portion of the tip, the channel having a diameter equal to or larger than a diameter of the received portion of the tip and smaller than a diameter of a locking ring radially disposed about the tip and located distally from the retaining cap, the retaining cap releasably engaged with the receiving end of the dental handpiece to retain the tip in the handpiece.

19. The motion-assisted dental scaling tool of claim 14, wherein the positioning element comprises a momentum transferring element, the handpiece comprising an inner cavity formed in a body having a service end and a tip receiving end, a spring disposed in the inner cavity between an electromagnet and a momentum plug, the momentum plug slideably engaged within the inner cavity between the tip receiving end and the electromagnet, the momentum plug comprising a magnetically active portion adjacent the spring and a tip attachment end receiving the mounting end of the tip.

20. The motion-assisted dental scaling tool of claim 14 in a powered handpiece system of a dental treatment system, further comprising:
a non-powered dental handpiece having a receiving end to releasably engage the mounting end of the dental tip, wherein the dental tip is interchangeable between the powered and non-powered handpieces.

* * * * *